United States Patent [19]

Hoffman et al.

[11] 4,172,131
[45] Oct. 23, 1979

[54] PESTICIDALLY ACTIVE N-(ALKOXY-ALKYLTHIO-THIOPHOS-PHORYL)-N-SUBSTITUTED-N-ARYLTHIO-FORMAMIDINES

[75] Inventors: Hellmut Hoffman, Wuppertal; Bernhard Homeyer, Leverkusen; Ingeborg Hammann, Cologne, all of Fed. Rep. of Germany

[73] Assignee: Bayer Aktiengesellschaft, Leverkusen, Fed. Rep. of Germany

[21] Appl. No.: 880,528

[22] Filed: Feb. 23, 1978

[30] Foreign Application Priority Data

Mar. 15, 1977 [DE] Fed. Rep. of Germany ....... 2711168

[51] Int. Cl.$^2$ .......................... A01N 9/36; C07F 9/02
[52] U.S. Cl. .................................... 424/211; 260/944
[58] Field of Search ........................ 260/944; 424/211

[56] References Cited

U.S. PATENT DOCUMENTS 3,949,022  4/1976  Hoffmann et al. ................... 424/211

Primary Examiner—Elbert L. Roberts
Assistant Examiner—Robert C. Whittenbaugh
Attorney, Agent, or Firm—Sprung, Felfe, Horn, Lynch & Kramer

[57] ABSTRACT

N-(Alkoxy-alkylthio-thiophosphoryl)-N'-substituted-N'-arylthio-formamidines of the formula

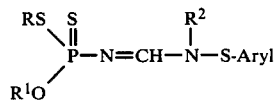

in which
R and R$^1$ each independently is alkyl,
R$^2$ is alkyl, cycloalkyl or alkenyl, and
Aryl is phenyl or phenyl substituted by at least one of alkyl and halogen,
which possess arthropodicidal and nematicidal properties.

9 Claims, No Drawings

PESTICIDALLY ACTIVE N-(ALKOXY-ALKYLTHIO-THIOPHOSPHORYL)-N-SUBSTITUTED-N-ARYLTHIO-FORMAMIDINES

The present invention relates to and has for its objects the provision of particular new N-(alkoxy-alkylthio-thiophosphoryl)-N'-substituted-N'-arylthio-formamidines which possess arthropodicidal and nematicidal properties, active compositions in the form of mixtures of such compounds with solid and liquid dispersible carrier vehicles, and methods for producing such compounds and for using such compounds in a new way especially for combating pests, e.g. arthropods and nematodes, with other and further objects becoming apparent from a study of the within specification and accompanying examples.

It is already known that certain phosphoryl-formamidines, for example N-(methoxy-methylthio-phosphoryl)-N',N'-diallylformamidine and N',N'-di-isobutyl-formamidine, are distinguished by an insecticidal and acaricidal activity (see German Offenlegungsschrift (German Published Specification) 2,216,552).

The present invention now provides, as new compounds, the N-thiophosphoryl-formamidines of the general formula

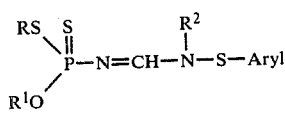 (I)

in which
R and $R^1$, which may be identical or different, each represent alkyl,
$R^2$ represents alkyl, cycloalkyl or alkenyl and
Aryl represents phenyl which may optionally carry one or more substituents selected independently from alkyl and halogen.

The compounds of the present invention are distinguished by powerful insecticidal, acaricidal and nematicidal properties.

Preferably, R represents straight-chain or branched alkyl with 1 to 6 (especially 1 to 4) carbon atoms, $R^1$ represents straight-chain or branched alkyl with 1 to 5 (especially 1 to 3) carbon atoms, $R^2$ represents straight-chain or branched alkyl with 1 to 6 (especially 1 to 4) carbon atoms, straight-chain or branched alkenyl with up to 6 (especially with up to 4) carbon atoms, or cycloalkyl with 3 to 8 (especially 5 or 6) carbon atoms and Aryl represents phenyl which can be optionally mono-substituted or polysubstituted by halogen (preferably chlorine and/or bromine).

Surprisingly, the N-thiophosphoryl-formamidines according to the invention exhibit a better insecticidal, acaricidal and nematicidal action than the previously known phosphoryl-formamidines of an analogous structure and the same type of action. The substances according to the present invention thus represent a true enrichment of the art.

The invention also provides a process for the preparation of an N-thiophosphoryl-formamidine of the formula (I), in which a dithiophosphoryl-formamidine of the general formula

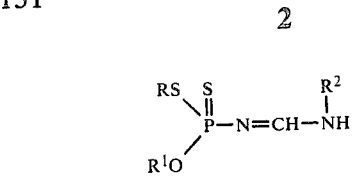 (II), in which
R, $R^1$ and $R^2$ have the meanings stated above, is reacted with an arylsulphenyl halide of the general formula

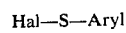 (III), in which
Aryl has the meaning stated above and
Hal represents halogen, preferably chlorine or bromine, optionally in the presence of an acid acceptor and optionally in the presence of a diluent or solvent.

If, for example, N-(methoxy-ethylthio-thiophosphoryl)-N'-ethyl-formamidine and benzenesulphenyl chloride are used as starting materials, the course of the reaction can be represented by the following equation:

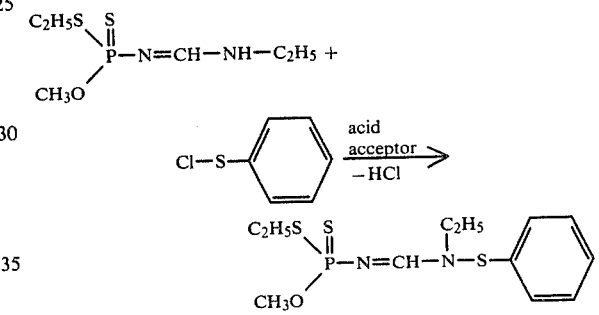

The dithiophosphoryl-formamidines (II) to be used as starting materials have not previously been described in the literature, but can be prepared, by processes known from the literature, from known dithiophosphoryliminoformic acid alkyl esters (see, for example, U.S. Pat. No. 3,903,207) and primary amines according to the following equation:

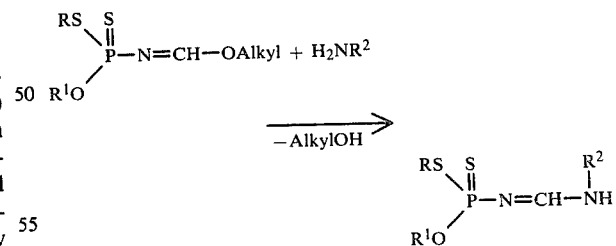

wherein
R, $R^1$ and $R^2$ have the meanings stated above and
Alkyl represents $C_1$–$C_4$ alkyl.

Examples of the formamidines (II) which may be mentioned are: N-(methoxy-methylthio-thiophosphoryl)-N'-methyl-formamidine, N-(methoxy-ethylthio-thiophosphoryl)-N'-methyl-formamidine, N-(methoxy-n-propylthio-thiophosphoryl)-N'-methyl-formamidine, N-(methoxy-iso-propylthio-thiophosphoryl)-N'-methyl-formamidine, N-(methoxy-n-butylthio-thiophosphoryl)-N'-methyl-formamidine, N-

(methoxy-sec.-butylthio-thiophosphoryl)-N'-methyl-formamidine, N-(methoxy-iso-butylthio-thiophosphoryl)-N'-methyl-formamidine, N-(ethoxy-methylthio-thiophosphoryl)-N'-methyl-formamidine, N-(ethoxy-ethylthio-thiophosphoryl)-N'-methyl-formamidine, N-(ethoxy-n-propylthio-thiophosphoryl)-N'-methyl-formamidine, N-(ethoxy-iso-propylthio-thiophosphoryl)-N'-methyl-formamidine, N-(ethoxy-n-butylthio-thiophosphoryl)-N'-methyl-formamidine, N-(ethoxy-sec.-butylthio-thiophosphoryl)-N'-methyl-formamidine, N-(ethoxy-iso-butylthio-thiophosphoryl)-N'-methyl-formamidine, N-(n-propoxy-methylthio-thiophosphoryl)-N'-methyl-formamidine, N-(n-propoxyethylthio-thiophosphoryl)-N'-methyl-formamidine, N-(n-propoxy-n-propylthio-thiophosphoryl)-N'-methyl-formamidine, N-(n-propoxy-iso-propylthio-thiophosphoryl)-N'-methyl-formamidine, N-(n-propoxy-n-butylthio-thiophosphoryl)-N'-methyl-formamidine, N-(n-propoxy-iso-butylthio-thiophosphoryl)-N'-methyl-formamidine, N-(n-propoxy-sec.-butylthio-thiophosphoryl)-N'-methyl-formamidine, N-(iso-propoxy-methylthio-thiophosphoryl)-N'-methyl-formamidine, N-(iso-propoxy-ethylthio-thiophosphoryl)-N'-methyl-formamidine, N-(iso-propoxy-n-propylthio-thiophosphoryl)-N'-methyl-formamidine, N-(iso-propoxy-iso-propylthio-thiophosphoryl)-N'-methyl-formamidine, N-(iso-propoxy-n-butylthio-thiophosphoryl)-N'-methyl-formamidine, N-(iso-propoxy-iso-butylthio-thiophosphoryl)-N'-methyl-formamidine, N-(iso-propoxy-sec.-butylthio-thiophosphoryl)-N'-methyl-formamidine, N-(methoxy-methylthio-thiophosphoryl)-N'-ethyl-formamidine, N-(methoxy-ethylthio-thiophosphoryl)-N'-ethyl-formamidine, N-(methoxy-n-propylthio-thiophosphoryl)-N'-ethyl-formamidine, N-(methoxy-iso-propylthio-thiophosphoryl)-N'-ethyl-formamidine, N-(methoxy-n-butylthio-thiophosphoryl)-N'-ethyl-formamidine, N-(methoxy-sec.-butylthio-thiophosphoryl)-N'-ethyl-formamidine, N-(methoxy-iso-butylthio-thiophosphoryl)-N'-ethyl-formamidine, N-(ethoxy-methylthio-thiophosphoryl)-N'-ethyl-formamidine, N-(ethoxy-ethylthio-thiophosphoryl)-N'-ethyl-formamidine, N-(ethoxy-n-propylthio-thiophosphoryl)-N'-ethyl-formamidine, N-(ethoxy-iso-propylthio-thiophosphoryl)-N'-ethyl-formamidine, N-(ethoxy-n-butylthio-thiophosphoryl)-N'-ethyl-formamidine, N-(ethoxy-sec.-butylthio-thiophosphoryl)-N'-ethyl-formamidine, N-(ethoxy-iso-butylthio-thiophosphoryl)-N'-ethyl-formamidine, N-(n-propoxy-methylthio-thiophosphoryl)-N'-ethyl-formamidine, N-(n-propoxy-ethylthio-thiophosphoryl)-N'-ethyl-formamidine, N-(n-propoxy-n-propylthio-thiophosphoryl)-N'-ethyl-formamidine, N-(n-propoxy-iso-propylthio-thiophosphoryl)-N'-ethyl-formamidine, N-(n-propoxy-n-butylthio-thiophosphoryl)-N'-ethyl-formamidine, N-(n-propoxy-iso-butylthio-thiophosphoryl)-N'-ethyl-formamidine, N-(n-propoxy-sec.-butylthio-thiophosphoryl)-N'-ethyl-formamidine, N-(iso-propoxy-methylthio-thiophosphoryl)-N'-ethyl-formamidine, N-(iso-propoxy-ethylthio-thiophosphoryl)-N'-ethyl-formamidine, N-(iso-propoxy-n-propylthio-thiophosphoryl)-N'-ethyl-formamidine, N-(iso-propoxy-iso-propylthio-thiophosphoryl)-N'-ethyl-formamidine, N-(iso-propoxy-n-butylthio-thiophosphoryl)-N'-ethyl-formamidine, N-(iso-propoxy-iso-butylthio-thiophosphoryl)-N'-ethyl-formamidine, N-(iso-propoxy-sec.-butylthio-thiophosphoryl)-N'-ethyl-formamidine, N-(methoxy-methylthio-thiophosphoryl)-N'-n-propyl-formamidine, N-(methoxy-ethylthio-thiophosphoryl)-N'-n-propylformamidine, N-(methoxy-n-propylthio-thiophosphoryl)-N'-n-propyl-formamidine, N-(methoxy-iso-propylthio-thiophosphoryl)-N'-n-propyl-formamidine, N-(methoxy-n-butylthio-thiophosphoryl)-N'-n-propyl-formamidine, N-(methoxy-sec.-butylthio-thiophosphoryl)-N'-n-propyl-formamidine, N-(methoxy-iso-butylthio-thiophosphoryl)-N'-n-propyl-formamidine, N-(ethoxy-methylthio-thiophosphoryl)-N'-n-propyl-formamidine, N-(ethoxy-ethylthio-thiophosphoryl)-N'-n-propyl-formamidine, N-(ethoxy-n-propylthio-thiophosphoryl)-N'-n-propyl-formamidine, N-(ethoxy-iso-propylthio-thiophosphoryl)-N'-n-propyl-formamidine, N-(ethoxy-n-butylthio-thiophosphoryl)-N'-n-propyl-formamidine, N-(ethoxy-sec.-butylthio-thiophosphoryl)-N'-n-propyl-formamidine, N-(ethoxy-iso-butylthio-thiophosphoryl)-N'-n-propyl-formamidine, N-(n-propoxy-methylthio-thiophosphoryl)-N'-n-propyl-formamidine, N-(n-propoxy-ethylthio-thiophosphoryl)-N'-n-propyl-formamidine, N-(n-propoxy-n-propylthio-thiophosphoryl)-N'-n-propyl-formamidine, N-(n-propoxy-iso-propylthio-thiophosphoryl)-N'-n-propyl-formamidine, N-(n-propoxy-n-butylthio-thiophosphoryl)-N'-n-propyl-formamidine, N-(n-propoxy-iso-butylthio-thiophosphoryl)-N'-n-propyl-formamidine, N-(n-propoxy-sec.-butylthio-thiophosphoryl)-N'-n-propyl-formamidine, N-(iso-propoxy-methylthio-thiophosphoryl)-N'-n-propyl-formamidine, N-(iso-propoxy-ethylthio-thiophosphoryl)-N'-n-propyl-formamidine, N-(iso-propoxy-n-propylthio-thiophosphoryl)-N'-n-propyl-formamidine, N-(iso-propoxy-iso-propylthio-thiophosphoryl)-N'-n-propyl-formamidine, N-(iso-propoxy-n-butylthio-thiophosphoryl)-N'-n-propyl-formamidine, N-(iso-propoxy-iso-butylthio-thiophosphoryl)-N'-n-propyl-formamidine, N-(iso-propoxy-sec.-butylthio-thiophosphoryl)-N'-n-propyl-formamidine, N-(methoxy-methylthio-thiophosphoryl)-N'-iso-propyl-formamidine, N-(methoxy-ethylthio-thiophosphoryl)-N'-iso-propyl-formamidine, N-(methoxy-n-propylthio-thiophosphoryl)-N'-iso-propyl-formamidine, N-(methoxy-iso-propylthio-thiophosphoryl)-N'-iso-propyl-formamidine, N-(methoxy-n-butylthio-thiophosphoryl)-N'-iso-propyl-formamidine, N-(methoxy-sec.-butylthio-thiophosphoryl)-N'-iso-propyl-formamidine, N-(methoxy-iso-butylthio-thiophosphoryl)-N'-iso-propyl-formamidine, N-(ethoxy-methylthio-thiophosphoryl)-N'-iso-propyl-formamidine, N-(ethoxy-ethylthio-thiophosphoryl)-N'-iso-propyl-formamidine, N-(ethoxy-n-propylthio-thiophosphoryl)-N'-iso-propyl-formamidine, N-(ethoxy-iso-propylthio-thiophosphoryl)-N'-iso-propyl-formamidine, N-(ethoxy-n-butylthio-thiophosphoryl)-N'-iso-propyl-formamidine, N-(ethoxy-iso-butylthio-thiophosphoryl)-N'-iso-propyl-formamidine, N-(ethoxy-sec.-butylthio-thiophosphoryl)-N'-iso-propyl-formamidine, N-(n-propoxy-methylthio-thiophosphoryl)-N'-iso-propyl-formamidine, N-(n-propoxy-ethylthio-thiophosphoryl)-N'-iso-propyl-formamidine, N-(n-propoxy-n-propylthio-thiophosphoryl)-N'-iso-propyl-formamidine, N-(n-propoxy-iso-propylthio-thiophosphoryl)-N'-iso-propyl-formamidine, N-(n-propoxy-n-butylthio-thiophosphoryl)-N'-iso-propyl-formamidine, N-(n-propoxy-iso-butylthio-thiophosphoryl)-N'-iso-propyl-formamidine, N-(n-propoxy-sec.-butylthio-thiophosphoryl)-N'-iso-propyl-formamidine, N-(iso-propoxy-methylthio-thiophosphoryl)-N'-iso-propyl-formamidine, N-(iso-propoxy-ethylthio-thiophosphoryl)-N'-iso-propyl-formamidine, N-(iso-propoxy-n-propylthio-thiophosphoryl)-N'-iso-propyl-formamidine, N-(iso-propoxy-iso-propylthio-thiophosphoryl)-N'-iso-propylformamidine, N-(iso-propoxy-n-butylthio-thiophosphoryl)-N'-iso-propyl-formamidine, N-(iso-propoxy-iso-butylthio-thiophosphoryl)-N'-iso-propyl-formamidine, N-(iso-propoxy-sec.-butylthio-thiophosphoryl)-N'-iso-propyl-formamidine, N-(methoxy-methylthio-thiophosphoryl)-N'-n-butyl-formamidine, N-(methoxy-ethylthio-thiophosphoryl)-N'-n-butyl-formamidine, N-(methoxy-n-propylthio-thiophosphoryl)-N'-n-butyl-formamidine, N-(methoxy-iso-propylthio-thiophosphoryl)-N'-n-butyl-formamidine, N-(methoxy-n-butylthio-thiophosphoryl)-N'-n-butyl-formamidine, N-(methoxy-sec.-butylthio-thiophosphoryl)-N'-n-butyl-formamidine, N-(methoxy-iso-butylthio-thiophosphoryl)-N'-n-butyl-formamidine, N-(ethoxy-methylthio-thiophosphoryl)-N'-n-butyl-formamidine, N-(ethoxy-ethylthio-thiophosphoryl)-N'-n-butyl-formamidine, N-ethoxy-n-propylthio-thiophosphoryl)-N'-n-butyl-formamidine, N-(ethoxy-iso-propylthio-thiophosphoryl)-N'-n-butyl-formamidine, N-(ethoxy-n-butylthio-thiophosphoryl)-N'-n-butyl-formamidine, N-(ethoxy-sec.-butylthio-thiophosphoryl)-N'-n-butylformamidine, N-ethoxy-iso-butylthio-thiophosphoryl)-N'-n-butyl-formamidine, N-(n-propoxy-methylthio-thiophosphoryl)-N'-n-butyl-formamidine, N-(n-propoxy-ethylthio-thiophosphoryl)-N'-n-butyl-formamidine, N-(n-propoxy-n-propylthio-thiophosphoryl)-N'-n-butyl-formamidine, N-(n-propoxy-iso-propylthio-thiophosphoryl)-N'-n-butyl-formamidine, N-(n-propoxy-n-butyl-thio-thiophosphoryl)-N'-n-butyl-formamidine, N-(n-propoxy-iso-butylthio-thiophosphoryl)-N'-n-butyl-formamidine, N-(n-propoxy-sec.-butylthio-thiophosphoryl)-N'-n-butyl-formamidine, N-(iso-propoxy-methylthio-thiophosphoryl)-N'-n-butyl-formamidine, N-(iso-propoxy-ethylthio-thiophosphoryl)-N'-n-butyl-formamidine, N-(iso-propoxy-n-propylthio-thiophosphoryl)-N'-n-butyl-formamidine, N-(iso-propoxy-iso-propylthio-thiophosphoryl)-N'-n-butyl-formamidine, N-(iso-propoxy-n-butylthio-thiophosphoryl)-N'-n-butyl-formamidine, N-(iso-propoxy-iso-butylthio-thiophosphoryl)-N'-n-butyl-formamidine, N-(iso-propoxy-sec.-butylthio-thiophosphoryl)-N'-n-butyl-formamidine, N-(methoxy-methylthio-thiophosphoryl)-N'-iso-butyl-formamidine, N-(methoxy-ethylthio-thiophosphoryl)-N'-iso-butyl-formamidine, N-(methoxy-n-propylthio-thiophosphoryl)-N'-iso-butyl-formamidine, N-(methoxy-iso-propylthio-thiophosphoryl)-N'-iso-butyl-formamidine, N-(methoxy-n-butylthio-thiophosphoryl)-N'-iso-butyl-formamidine, N-(methoxy-sec.-butylthio-thiophosphoryl)-N'-iso-butyl-formamidine, N-(methoxy-iso-butylthio-thiophosphoryl)-N'-iso-butyl-formamidine, N-(ethoxy-methylthio-thiophosphoryl)-N'-iso-butyl-formamidine, N-(ethoxy-ethylthio-thiophosphoryl)-N'-iso-butyl-formamidine, N-(ethoxy-n-propylthio-thiophosphoryl)-N'-iso-butyl-formamidine, N-(ethoxy-iso-propylthio-thiophosphoryl)-N'-iso-butyl-formamidine, N-(ethoxy-n-butylthio-thiophosphoryl)-N'-iso-butyl-formamidine, N-(ethoxy-sec.-butylthio-thiophosphoryl)-N'-iso-butyl-formamidine, N-(ethoxy-iso-butylthio-thiophosphoryl)-N'-iso-butyl-formamidine, N-(n-propoxy-methylthio-thiophosphoryl)-N'-iso-butyl-formamidine, N-(n-propoxy-ethylthio-thiophosphoryl)-N'-iso-butyl-formamidine, N-(n-propoxy-n-propylthio-thiophosphoryl)-N'-iso-butyl-formamidine, N-(n-propoxy-iso-propylthio-thiophosphoryl)-N'-iso-butyl-formamidine, N-(n-propoxy-n-butylthio-thiophosphoryl)-N'-iso-butyl-formamidine, N-(n-propoxy-iso-butylthio-thiophosphoryl)-N'-iso-butyl-formamidine, N-(n-propoxy-sec.-butylthio-thiophosphoryl)-N'-iso-butyl-formamidine, N-(iso-propoxy-methylthio-thiophosphoryl)-N'-iso-butyl-formamidine, N-(iso-propoxy-ethylthio-thiophosphoryl)-N'-iso-butyl-formamidine, N-(iso-propoxy-n-propylthio-thiophosphoryl)-N'-iso-butyl-formamidine, N-(iso-propoxy-iso-propylthio-thiophosphoryl)-N'-iso-butyl-formamidine, N-(iso-propoxy-n-butylthio-thiophosphoryl)-N'-iso-butyl-formamidine, N-(iso-propoxy-iso-butylthio-thiophosphoryl)-N'-iso-butyl-formamidine, N-(iso-propoxy-sec.-butylthio-thiophosphoryl)-N'-iso-butyl-formamidine, N-(methoxy-methylthio-thiophosphoryl)-N'-sec.-butyl-formamidine, N-(methoxy-ethylthio-thiophosphoryl)-N'-sec.-butyl-formamidine, N-(methoxy-n-propylthio-thiophosphoryl)-N'-sec.-butyl-formamidine, N-(methoxy-iso-propylthio-thiophosphoryl)-N'-sec.-butyl-formamidine, N-(methoxy-n-butylthio-thiophosphoryl)-N'-sec.-butyl-formamidine, N-(methoxy-sec.-butylthio-thiophosphoryl)-N'-sec.-butyl-formamidine, N-(methoxy-iso-butylthio-thiophosphoryl)-N'-sec.-butyl-formamidine, N-(ethoxy-methylthio-thiophosphoryl)-N'-sec.-butyl-formamidine, N-(ethoxy-ethylthio-thiophosphoryl)-N'-sec.-butyl-formamidine, N-(ethoxy-n-propylthio-thiophosphoryl)-N'-sec.-butyl-formamidine, N-(ethoxy-iso-propylthio-thiophosphoryl)-N'-sec.-butyl-formamidine, N-(ethoxy-n-butylthio-thiophosphoryl)-N'-sec.-butyl-formamidine, N-(ethoxy-sec.-butylthio-thiophosphoryl)-N'-sec.-butyl-formamidine, N-(ethoxy-iso-butylthio-thiophosphoryl)-N'-sec.-butyl-formamidine, N-(n-propoxy-methylthio-thiophosphoryl)-N'-sec.-butyl-formamidine, N-(n-propoxy-ethylthio-thiophosphoryl)-N'-sec.-butyl-formamidine, N-(n-propoxy-n-propylthio-thiophosphoryl)-N'-sec.-butyl-formamidine, N-(n-propoxy-iso-propylthio-thiophosphoryl)-N'-sec.-butyl-formamidine, N-(n-propoxy-n-butylthio-thiophosphoryl)-N'-sec.-butyl-formamidine, N-(n-propoxy-iso-butylthio-thiophosphoryl)-N'-sec.-butyl-formamidine, N-(n-propoxy-sec.-butylthio-thiophosphoryl)-N'-sec.-butyl-formamidine, N-(iso-propoxy-methylthio-thiophosphoryl)-N'-sec.-butyl-formamidine, N-(iso-propoxy-ethylthio-thiophosphoryl)-N'-sec.-butyl-formamidine, N-(iso-propoxy-n-propylthio-thiophosphoryl)-N'-sec.-butyl-formamidine, N-(iso-propoxy-iso-propylthio-thiophosphoryl)-N'-sec.-butyl-formamidine, N-(iso-propoxy-n-butylthio-thiophosphoryl)-N'-sec.-butyl-formamidine, N-(iso-propoxy-iso-butylthio-thiophosphoryl)-N'-sec.-butyl-formamidine, N-(iso-propoxy-sec.-butylthio-thiophosphoryl)-N'-sec.-butyl-formamidine, N-(methoxy-methylthio-thiophosphoryl)-N'-allyl-formamidine, N-(methoxy-ethylthio-thiophosphoryl)-N'-allyl-formamidine, N-(methoxy-n-propylthio-thiophosphoryl)-N'-allyl-formamidine, N-(methoxy-iso-propylthio-thiophosphoryl)-N'-allyl-formamidine, N-(methoxy-n-butylthio-thiophosphoryl)-N'-allyl-formamidine, N-(methoxy-sec.-butylthio-thiophosphoryl)-N'-allyl-formamidine, N-(methoxy-iso-butylthio-thiophosphoryl)-N'-allyl-formamidine, N-(ethoxy-methylthio-thiophosphoryl)-N'-allyl-formamidine, N-(ethoxy-ethylthio-thiophosphoryl)-N'-allyl-formamidine, N-(ethoxy-n-propylthio-thiophosphoryl)-N'-allyl-formamidine, N-(ethoxy-iso-propylthio-thiophosphoryl)-N'-allyl-formamidine, N-(ethoxy-n-butylthio-thiophosphoryl)-N'-allyl-formamidine, N-(ethoxy-sec.-butylthio-thiophosphoryl)-N'-allyl-formamidine, N-(ethoxy-iso-butylthio-thiophosphoryl)-N'-allyl-formamidine, N-(n-propoxy-methylthio-thiophosphoryl)-N'-allyl-formamidine, N-(n-propoxy-ethylthio-thiophosphoryl)-N'-allyl-formamidine, N-(n-propoxy-n- propylthio-thiophosphoryl)-N'-allyl-formamidine, N-(n-propoxy-iso-propylthio-thiophosphoryl)-N'-allyl-formamidine, N-(n-propoxy-n-butylthio-thiophosphoryl)-N'-allyl-formamidine, N-(n-propoxy-iso-butylthio-thiophosphoryl)-N'-allyl-formamidine, N-(n-propoxy-sec.-butylthio-thiophosphoryl)-N'-allyl-formamidine, N-(iso-propoxy-methylthio-thiophosphoryl)-N'-allyl-formamidine, N-(iso-propoxy-ethylthio-thiophosphoryl)-N'-allyl-formamidine, N-(iso-propoxy-n-propylthio-thiophosphoryl)-N'-allyl-formamidine, N-(iso-propoxy-iso-propylthio-thiophosphoryl)-N'-allyl-formamidine, N-(iso-propoxy-n-butylthio-thiophosphoryl)-N'-allyl-formamidine, N-(iso-propoxy-iso-butylthio-thiophosphoryl)-N'-allyl-formamidine, N-(iso-propoxy-sec.-butylthio-thiophosphoryl)-N'-allyl-formamidine, N-(methoxy-methylthio-thiophosphoryl)-N'-propenyl-formamidine, N-(methoxy-ethylthio-thiophosphoryl)-N'-propenyl-formamidine, N-(methoxy-n-propylthio-thiophosphoryl)-N'-propenyl-formamidine, N-(methoxy-iso-propylthio-thiophosphoryl)-N'-propenyl-formamidine, N-(methoxy-n-butylthio-thiophosphoryl)-N'-propenyl-formamidine, N-(methoxy-iso-butylthio-thiophosphoryl)-N'-propenyl-formamidine, N-(methoxy-sec.-butylthio-thiophosphoryl)-N'-propenyl-formamidine, N-(ethoxy-methylthio-thiophosphoryl)-N'-propenyl-formamidine, N-(ethoxy-ethylthio-thiophosphoryl)-N'-propenyl-formamidine, N-(ethoxy-n-propylthio-thiophosphoryl)-N'-propenyl-formamidine, N-(ethoxy-iso-propylthio-thiophosphoryl)-N'-propenyl-formamidine, N-(ethoxy-n-butylthio-thiophosphoryl)-N'-propenyl-formamidine, N-(ethoxy-iso-butylthio-thiophosphoryl)-N'-propenyl-formamidine, N-(ethoxy-sec.-butylthio-thiophosphoryl)-N'-propenylformamidine, N-(n-propoxy-methylthio-thiophosphoryl)-N'-propenyl-formamidine, N-(n-propoxy-ethylthio-thiophosphoryl)-N'-propenyl-formamidine, N-(n-propoxy-n-propylthiothiophosphoryl)-N'-propenyl-formamidine, N-(n-propoxy-isopropylthio-thiophosphoryl)-N'-propenyl-formamidine, N-(n-propoxy-n-butylthio-thiophosphoryl)-N'-propenyl-formamidine, N-(n-propoxy-iso-butylthio-thiophosphoryl)-N'-propenylformamidine, N-(n-propoxy-sec.-butylthio-thiophosphoryl)-N'-propenyl-formamidine, N-(iso-propoxy-methylthio-thiophosphoryl)-N'-propenyl-formamidine, N-(iso-propoxy-ethylthiothiophosphoryl)-N'-propenyl-formamidine, N-(iso-propoxy-n-propylthio-thiophosphoryl)-N'-propenyl-formamidine, N-(iso-propoxy-iso-propylthio-thiophosphoryl)-N'-propenyl-formamidine, N-(iso-propoxy-n-butylthio-thiophosphoryl)-N'-propenyl-formamidine, N-(iso-propoxy-iso-butylthio-thiophosphoryl)-N'-propenyl-formamidine, N-(iso-propoxy-sec.-butylthio-thiophosphoryl)-N'-propenyl-formamidine, N-(methoxy-methylthio-thiophosphoryl)-N'-cyclopentyl-formamidine, N-(methoxy-ethylthio-thiophosphoryl)-N'-cyclopentyl-formamidine, N-(methoxy-n-propylthio-thiophosphoryl)-N'-cyclopentyl-formamidine, N-(methoxy-iso-propylthio-thiophosphoryl)-N'-cyclopentyl-formamidine, N-(methoxy-n-butylthio-thiophosphoryl)-N'-cyclopentyl-formamidine, N-(methoxy-iso-butylthio-thiophosphoryl)-N'-cyclopentyl-formamidine, N-(methoxy-sec.-butylthio-thiophosphoryl)-N'-cyclopentyl-formamidine, N-(ethoxy-methylthio-thiophosphoryl)-N'-cyclopentyl-formamidine, N-(ethoxyethylthio-thiophosphoryl)-N'-cyclopentyl-formamidine, N-(ethoxy-n-propylthio-thiophosphoryl)-N'-cyclopentyl-formamidine, N-(ethoxy-iso-propylthio-thiophosphoryl)-N'-cyclopentyl-formamidine, N-(ethoxy-n-butylthio-thiophosphoryl)-N'-cyclopentyl-formamidine, N-(ethoxy-iso-butylthio-thiophosphoryl)-N'-cyclopentyl-formamidine, N-(ethoxy-sec.-butylthio-thiophosphoryl)-N'-cyclopentyl-formamidine, N-(n-propoxy-methylthio-thiophosphoryl)-N'-cyclopentyl-formamidine, N-(n-propoxy-ethylthio-thiophosphoryl)-N'-cyclopentyl-formamidine, N-(n-propoxy-n-propylthio-thiophosphoryl)-N'-cyclopentyl-formamidine, N-(n-propoxy-iso-propylthio-thiophosphoryl)-N'-cyclopentyl-formamidine, N-(n-propoxy-n-butylthio-thiophosphoryl)-N'-cyclopentyl-formamidine, N-(n-propoxy-iso-butylthio-thiophosphoryl)-N'-cyclopentyl-formamidine, N-(n-propoxy-sec.-butylthio-thiophosphoryl)-N'-cyclopentyl-formamidine, N-(iso-popoxy-methylthio-thiophosphoryl)-N'-cyclopentyl-formamidine, N-(iso-propoxy-ethylthio-thiophosphoryl)-N'-cyclopentyl-formamidine, N-(iso-propoxy-n-propylthio-thiophosphoryl)-N'-cyclopentyl-formamidine, N-(iso-propoxy-iso-propylthio-thiophosphoryl)-N'-cyclopentyl-formamidine, N-(iso-propoxy-n-butylthio-thiophosphoryl)-N'-cyclopentyl-formamidine, N-(iso-propoxy-iso-butylthio-thiophosphoryl)-N'-cyclopentyl-formamidine, N-(iso-propoxy-sec.-butylthio-thiophosphoryl)-N'-cyclopentyl-formamidine, N-(methoxy-methylthio-thiophosphoryl)-N'-cyclohexyl-formamidine, N-(methoxy-ethylthio-thiophosphoryl)-N'-cyclohexyl-formamidine, N-(methoxy-n-propylthio-thiophosphoryl)-N'-cyclohexyl-formamidine, N-(methoxy-iso-propylthio-thiophosphoryl)-N'-cyclohexyl-formamidine, N-(methoxy-n-butylthio-thiophosphoryl)-N'-cyclohexyl-formamidine, N-(methoxy-sec.-butylthio-thiophosphoryl)-N'-cyclohexyl-formamidine, N-(methoxy-iso-butylthio-thiophosphoryl)-N'-cyclohexyl-formamidine, N-(ethoxy-methylthio-thiophosphoryl)-N'-cyclohexyl-formamidine, N-(ethoxy-ethylthio-thiophosphoryl)-N'-cyclohexyl-formamidine, N-(ethoxy-n-propylthio-thiophosphoryl)-N'-cyclohexyl-formamidine, N-(ethoxy-iso-propylthio-thiophosphoryl)-N'-cyclohexyl-formamidine, N-(ethoxy-n-butylthio-thiophosphoryl)-N'-cyclohexyl-formamidine, N-(ethoxy-iso-butylthio-thiophosphoryl)-N'-cyclohexyl-formamidine, N-(ethoxy-sec.-butylthio-thiophosphoryl)-N'-cyclohexyl-formamidine, N-(n-propoxy-methylthio-thiophosphoryl)-N'-cyclohexyl-formamidine, N-(n-propoxy-ethylthio-thiophosphoryl)-N'-cyclohexyl-formamidine, N-(n-propoxy-n-propylthiothiophophoryl)-N'-cyclohexyl-formamidine, N-(n-propoxy-iso-propylthio-thiophosphoryl)-N'-cyclohexyl-formamidine, N-(n-propoxy-n-butylthio-thiophosphoryl)-N'-cyclohexyl-formamidine, N-(n-propoxy-iso-butylthio-thiophosphoryl)-N'-cyclohexyl-formamidine, N-(n-propoxy-sec.-butylthio-thiophosphoryl)-N'-cyclohexyl-formamidine, N-(iso-propoxy-methylthio-thiophosphoryl)-N'-cyclohexyl-formamidine, N-(iso-propoxy-ethylthio-thiophosphoryl)-N'-cyclohexyl-formamidine, N-(iso-propoxy-n-propylthio-thiophosphoryl)-N'-cyclohexyl-formamidine, N-(iso-propoxy-iso-propylthio-thiophosphoryl)-N'-cyclohexyl-formamidine, N-(iso-propoxy-n-butylthio-thiophosphoryl)-N'-cyclohexyl-formamidine, N-(iso-propoxy-iso-butylthio-thiophosphoryl)-N'-cyclohexyl-formamidine and N-(iso-propoxy-sec.-butylthio-thiophosphoryl)-N'-cyclohexyl-formamidine.

The arylsulphenyl halides (III) which are also to be used as starting substances are known.

Examples of these which may be mentioned are: benzenesulphenyl chloride, 4-chlorobenzenesulphenyl chloride, 4-bromobenzenesulphenyl chloride, 2,4-dichlorobenzenesulphenyl chloride, 3,4-dichlorobenzenesulphenyl chloride, 2-chlorobenzenesulphenyl chloride and 2-bromobenzenesulphenyl chloride, and the corresponding bromides.

The process for the preparation of the compounds according to the invention is preferably carried out using a suitable solvent or diluent. Possible solvents or diluents are virtually all the inert organic solvents, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane ketones, for example acetone, methyl ethyl ketone, methyl isopropyl ketone and methyl isobutyl ketone; and nitriles, such as acetonitrile and propionitrile.

Acid acceptors which can be used are all the customary acid-binding agents. Alkali metal carbonates and alcoholates, such as sodium carbonate and potassium carbonate, sodium methylate or ethylate and potassium methylate or ethylate, and furthermore aliphatic, aromatic or heterocyclic amines, for example triethylamine, trimethylamine, dimethylaniline, dimethylbenzylamine and pyridine, have proved particularly suitable.

The reaction temperature can be varied within a relatively wide range. In general, the reaction is carried out at from 0° to 90° C., preferably at from 0° to 25° C.

In general, the reaction is allowed to proceed under normal pressure.

The new compounds are obtained in the form of oils, which in a number of cases cannot be distilled without decomposition, but are freed from the last volatile constituents by so-called "incipient distillation", that is to say by prolonged heating under reduced pressure to moderately elevated temperatures, and are purified in this manner. They are characterized by the refractive index.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium purctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomya spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic means, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

Such active compounds may be employed alone or in the form of mixtures with one another and/or with such solid and/or liquid dispersible carrier vehicles and/or with other known compatible active agents, especially plant protection agents, such as other arthropodicides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. arthropods and nematodes, which comprises applying to at least one of correspondingly (a) such arthropods, (b) such nematodes, and (c) the corresponding habitat thereof, i.e. the locus to be protected, e.g. to a growing crop, to an area where a crop is to be grown or to a domestic animal, a correspondingly combative or toxic amount, i.e. an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of

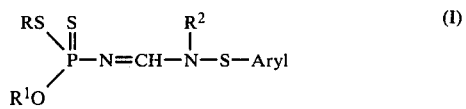

could be prepared analogously:

TABLE 1

| Compound No. | R | R¹ | R² | Aryl | Refractive index: |
|---|---|---|---|---|---|
| 2 | n-C₃H₇ | CH₃ | C₃H₇-iso | phenyl | $n_D^{24}$:1.5891 |
| 3 | n-C₃H₇ | CH₃ | cyclohexyl-H | phenyl | $n_D^{24}$:1.5980 |
| 4 | n-C₃H₇ | CH₃ | —CH₂—CH=CH₂ | phenyl | $n_D^{24}$:1.5979 |
| 5 | n-C₃H₇ | C₂H₅ | C₃H₇-iso | 4-Cl-phenyl | $n_D^{24}$:1.5916 |
| 6 | n-C₄H₉ | C₂H₅ | C₃H₇-iso | phenyl | $n_D^{24}$:1.5758 |
| 7 | n-C₄H₉ | C₂H₅ | CH₃ | 4-Cl-phenyl | $n_D^{24}$:1.5909 | the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

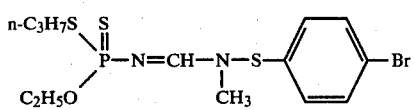

22 g (0.1 mol) of 4-bromobenzenesulphenyl chloride were allowed to run into a solution of 200 ml of toluene, 24 g (0.1 mol) of N-(ethoxy-n-propylthio-thiophosphoryl)-N'-methyl-formamidine and 11 g of triethylamine at 0°–5° C., while stirring and cooling. The mixture was stirred for a further 3 hours at room temperature and filtered, the solvent was removed from the filtrate in vacuo and the residue was distilled under a mercury vacuum pump. This gave 36 g (84% of theory) of N-(ethoxy-n-propylthio-thiophosphoryl)-N'-methyl-N'-4-bromophenylthio-formamidine having a refractive index $n_D^{22}$ of 1.6149.

The following compounds of the general formula

The insecticidal, acaricidal and nematicidal activity of the compounds of this invention is illustrated by the following examples in which the compounds according to the present invention are each identified by the number (given in brackets) from preparative example 1 hereinabove.

The known comparison compounds are identified as follows:

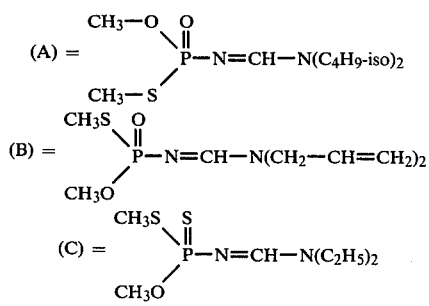

EXAMPLE 2

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 2

| Active compound | (Nematicides) *Meloidogyne incognita* Degree of destruction in % at an active compound concentration of 5 ppm |
| --- | --- |
| (A) | 0 |
| (1) | 100 |
| (5) | 100 |
| (2) | 100 |
| (6) | 100 |
| (4) | 100 |

EXAMPLE 3

Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test animals after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

The active compounds, the amounts used and the results can be seen from the following table:

Table 3

| Active compound | (Root-systemic action) *Phaedon cochleariae* larvae Degree of destruction in % at an active compound concentration of 20 ppm |
| --- | --- |
| (A) | 0 |
| (1) | 100 |
| (5) | 100 |

EXAMPLE 4

Drosophila test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% meant that all of the flies were killed; 0% meant that none of the flies were killed.

The active compounds, the concentrations of the active compounds, the evaluation times and the results can be seen from the following table:

Table 4

| Active compounds | (Insects which damage plants) Drosophila test Active compound concentration in % | Degree of destruction in % after 1 day |
| --- | --- | --- |
| (B) | 0.1 | 50 |
|  | 0.01 | 0 |
| (2) | 0.1 | 100 |
|  | 0.01 | 100 |
| (4) | 0.1 | 100 |
|  | 0.01 | 90 |
| (3) | 0.1 | 100 |
|  | 0.01 | 100 |

EXAMPLE 5

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 5

| Active compounds | (Mites which damage plants) Tetranychus test | |
|---|---|---|
| | Active compound concentration in % | Degree of destruction in % after 2 days |
| (C) | 0.1 | 99 |
| | 0.01 | 0 |
| (B) | 0.1 | 100 |
| | 0.01 | 0 |
| (4) | 0.1 | 100 |
| | 0.01 | 100 |
| (2) | 0.1 | 100 |
| | 0.01 | 99 |
| (5) | 0.1 | 100 |
| | 0.01 | 99 |
| (6) | 0.1 | 100 |
| | 0.01 | 90 |
| (7) | 0.1 | 100 |
| | 0.01 | 98 |
| (1) | 0.1 | 100 |
| | 0.01 | 100 |

It will be appreciated that the instant specification and examples are set forth by way of illustration and not limitation, and that various modifications and changes may be made without departing from the spirit and scope of the present invention.

What is claimed is:

1. An N-(alkoxy-alkylthio-thiophosphoryl)-N'-substituted-N'-arylthio-formamidine of the formula

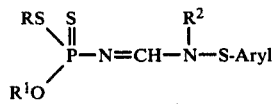

in which
R is alkyl with 1 to 6 carbon atoms,
R¹ is alkyl with 1 to 5 carbon atoms
R² is alkyl with 1 to 6 carbon atoms, alkenyl with up to 6 carbon atoms, or cycloalkyl with 3 to 8 carbon atoms, and
Aryl is phenyl or chlorophenyl.

2. A compound according to claim 1, wherein such compound is N-(ethoxy-n-propylthio-thiophosphoryl)-N'-methyl-N'-4-bromophenylthio-formamidine of the formula

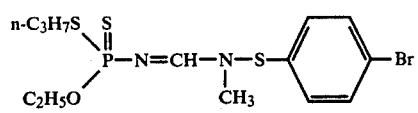

3. A compound according to claim 1, wherein such compound is N-(methoxy-n-propylthio-thiophosphoryl)-N'-iso-propyl-N'-phenylthio-formamidine of the formula

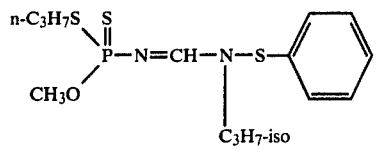

4. A compound according to claim 1, wherein such compound is N-(methoxy-n-propylthio-thiophosphoryl)-N'-allyl-N'-phenylthio-formamidine of the formula

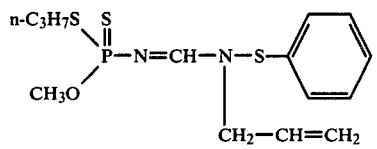

5. A compound according to claim 1, wherein such compound is N-(ethoxy-n-propylthio-thiophosphoryl)-N'-iso-propyl-N'-4-chlorophenylthio-formamidine of the formula

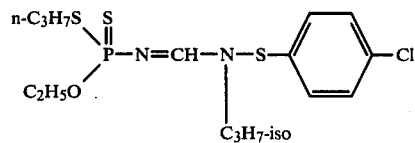

6. A compound according to claim 1, wherein such compound is N-(ethoxy-n-butylthio-thiophosphoryl)-N'-iso-propyl-N'-phenylthio-formamidine of the formula

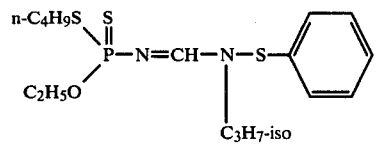

7. An arthropodicidal or nematicidal composition containing as active ingredient an arthropodicidally or nematicidally effective amount of a compound according to claim 1 in admixture with a diluent.

8. A method of combating arthropods or nematodes which comprises applying to the arthropods or nematodes, or to a habitat therof, an arthropodicidally or nematicidally effective amount of a compound according to claim 1.

9. The method according to claim 8, in which said compound is
N-(ethoxy-n-propylthio-thiophosphoryl)-N'-methyl-N'-4-bromophenylthio-formamidine,
N-(methoxy-n-propylthio-thiophosphoryl)-N'-isopropyl N'-phenylthio-formamidine
N-(methoxy-n-propylthio-thiophosphoryl)-N'-allyl-N'-phenylthio-formamidine,
N-(ethoxy-n-propylthio-thiophosphoryl)-N'-iso-propyl-N'-4-chlorophenylthio-formamidine, or
N-(ethoxy-n-butylthio-thiophosphoryl)-N'-iso-propyl-N'-phenylthio-formamidine.

* * * * *